US00PP11308P

United States Patent [19]

Noack

[11] Patent Number: Plant 11,308

[45] Date of Patent: Mar. 21, 2000

[54] GROUND COVER ROSE PLANT NAMED 'NOARE'

[76] Inventor: Reinhard Noack, Im Fenne 54, 33334 Gütersloh, Germany

[21] Appl. No.: 09/119,583

[22] Filed: Jul. 21, 1998

[30] Foreign Application Priority Data

Nov. 13, 1997 [DE] Germany ..... ROS 1543

[51] Int. Cl.[7] ..... A01H 5/00

[52] U.S. Cl. ..... Plt./101

[58] Field of Search ..... Plt./101, 102, 108, Plt./115, 150, 151

*Primary Examiner*—Howard J. Locker

*Attorney, Agent, or Firm*—Burns, Doane, Swecker & Mathis, L.L.P.

[57] ABSTRACT

A new and distinct variety of ground cover rose plant is provided which forms substantially continuously throughout the season long-lasting bright velvet red blossoms. The blossoms tend to open on a reliable basis and remain attractive upon aging. The new variety exhibits a compact, spreading and overhanging growth habit that renders it suitable for growing as an ornamental ground cover in the landscape and home garden. The foliage is glossy and contrasts well with the bright velvet red blossoms. The reproductive organs and pollen provide a bright yellow coloration at the center of each fully open blossom. The petals drop off cleanly as the blossoms mature. The new variety propagates well from cuttings and by budding and exhibits an excellent resistance to blackspot, mildew, and rust.

2 Drawing Sheets

SUMMARY OF THE INVENTION

Ground cover rose plants are known and are being used to advantage in an increasing number of landscape plans and home gardens. However, there remains a need for additional varieties of ground cover roses with the demand being the greatest for those having highly attractive blossoms in combination with good disease resistance. The new variety of ground cover rose plant of the present invention was created at Gütersloh, Germany by artificial pollination wherein two parents were crossed which previously had been studied in the hope that they would contribute the desired characteristics. The female parent(i.e., the seed parent) was the 'Ricarda' variety (non-patented in the United States). Such 'Ricarda' variety possesses deep salmon pink semi-double blossoms. The male parent (i.e., the pollen parent) was an unnamed seedling that included the 'Flower Carpet' variety (U.S. Plant Pat. No. 7,282) in its parentage. The parentage of the new variety of the present invention can be summarized as follows:

'Ricarda'×Unnamed Seedling.

The seeds resulting from the above pollination were sown and small plants were obtained which physically and biologically differ from each other. Selective study resulted in the identification of a single plant of the new variety that initially was identified as No. 1039-89.

It is found that the new ground cover rose plant of the present invention possesses the following combination of characteristics:

(a) forms attractive dark velvet red blossoms with bright yellow pollen and reproductive organs at the center,
(b) exhibits a low, dense, compact and spreading growth habit,
(c) forms attractive glossy foliage that contrasts well with the dark velvet red blossoms,
(d) exhibits excellent disease resistance with respect to blackspot, mildew, and rust, and
(e) is particularly suited for growing as attractive ornamentation in the landscape.

The new variety well meets the needs of the horticultural industry and can be grown to advantage as attractive ornamentation in parks, gardens, public areas, and residential landscapes. The new variety of the present invention from 1989 to date has been found to readily undergo asexual reproduction in Germany by the use of cuttings and by budding. Such asexual reproduction as performed in Germany has shown that the characteristics of the new variety are homogeneous and stable and are strictly transmissible from one generation to another. The new variety has been named the 'Noare' variety.

BRIEF DESCRIPTION OF THE PHOTOGRAPHS

The accompanying photographs show as nearly true as it is reasonably possible to make the same, in color illustrations of this character, typical specimens of the new variety while growing in the landscape. The illustrated rose plants were photographed during July, 1997, while growing in the field at Gütersloh, Germany. Such plants had been budded approximately one year earlier. The blossoms retain their attractive appearance even upon aging (as illustrated).

DETAILED DESCRIPTION

Figure 1:
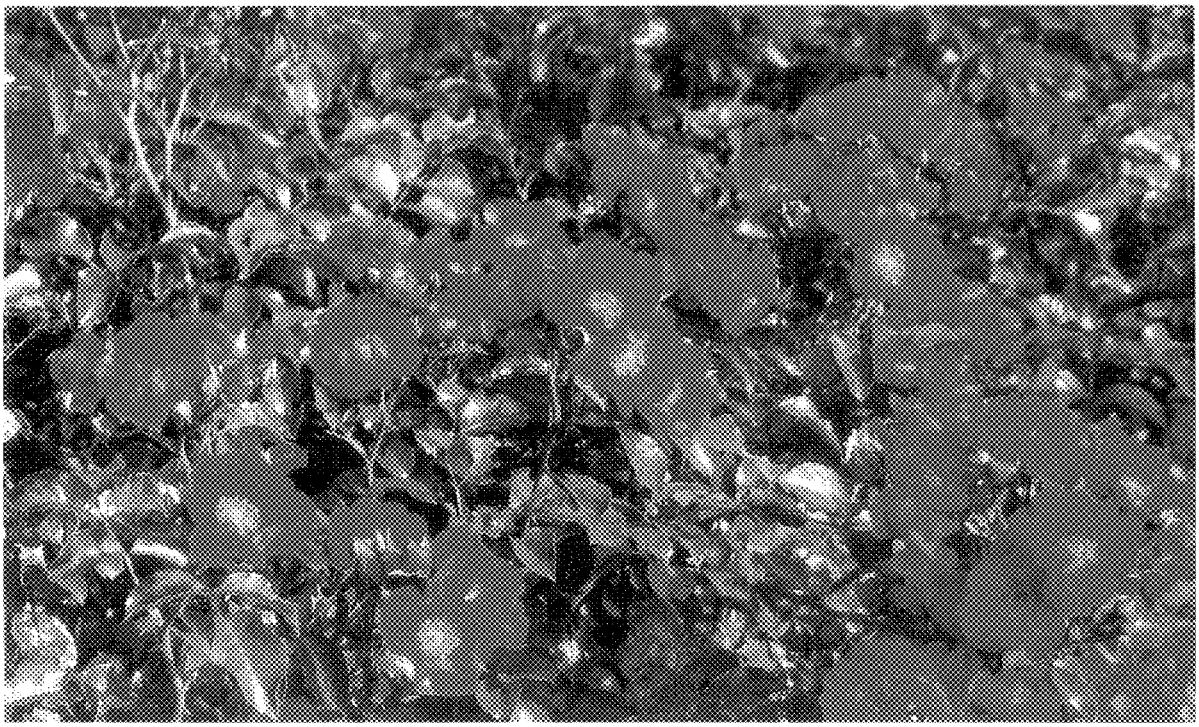
FIG. 1 illustrates a profusion of glossy dark green foliage and buds and blossoms in various stages of opening.
Figure 2:
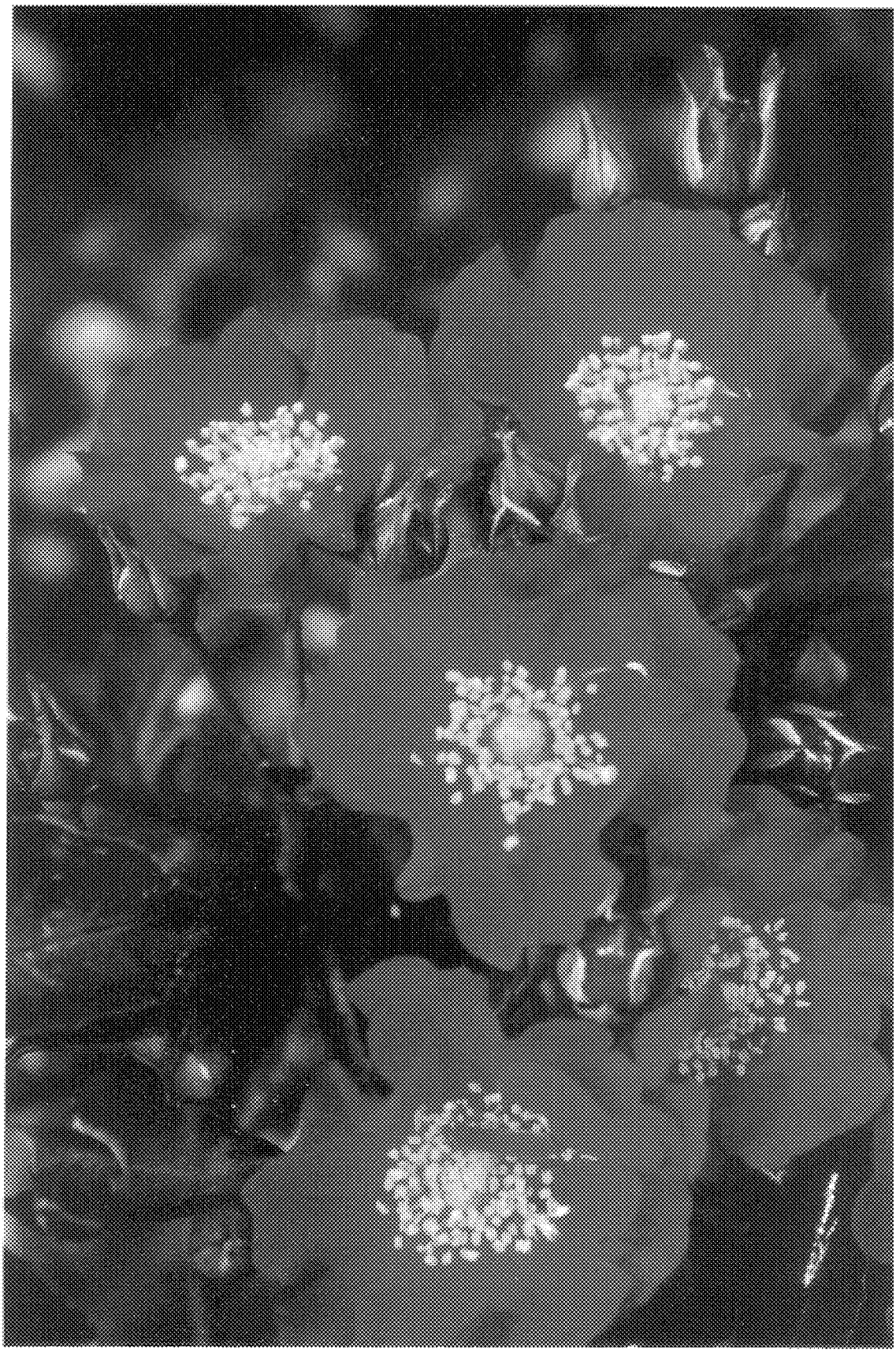
FIG. 2 illustrates a closer view of the blossoms wherein the bright velvet red coloration is shown to contrast nicely with the bright yellow stigmas and pollen.

The chart used in the identification of the colors is that of The Royal Horticultural Society (R.H.S. Colour Chart) of London, England. Color terminology in common terms sometimes is included as an aid to the reader. The description is based on the observation of specimens of the new variety while growing outdoors during July at Gütersloh, Germany.

Class: Ground cover.

Parentage:

*Female.*—'Ricarda' (non-patented in the United States).

*Male.*—'Unnamed Seedling' (non-patented in the United States) having a parentage that includes the 'Flower Carpet' variety (U.S. Plant Pat. No. 7,282).

Plant:

*Form.*—Vigorous, compact and spreading, well covers the ground, and assumes an ideal ground cover growth habit.

*Size.*—A typical one year-old plant growing in the landscape commonly assumes a height of approximately 40 to 50 cm. and a width of approximately 50 cm., and a typical two year-old plant growing in the landscape commonly assumes a height of approximately 70 cm, and a width of approximately 70 cm.

Branches:

*Color.*—Young stems: light green, Green Group 137B, and with a smooth surface. Adult wood: medium dark green, Green Group 136B, darker than young stems, and with a smooth surface.

*Thorns.*—Size: medium, approximately 6 mm. in length on average, and slightly curved downward. Position: irregular. Color: initially light red-brown, near Red Group 47A, and changing to dark brown with maturity. Quantity: average.

Leaves:

*Stiples.*—Dark green, Green Group 136B, in coloration.

*Petioles.*—Near Green Group 138A in coloration.

*Leaflets.*—Number: commonly 5. Configuration: oval and pointed. Quantity: very abundant. Size: medium to large approximately 3 cm. in length and about 1.5 cm in width. Serration: slightly serrate. Color (young foliage): Upper surface: light green, Green Group 138A. Under surface: lighter green than upper surface, near Green Group 138B. Color (adult foliage): Upper surface: slightly darker than young foliage, Green Group 135A. Under surface: somewhat darker green than new foliage, Green Group 135B. General appearance: dense, green foliage that is glossy on the upper surface and matte on the under surface. Texture: leathery. Stipules: dark green in coloration, near Green Group 136B.

Inflorescence:

*Number of flowers.*—Numerous and commonly in large sprays of approximately 20 to 25 blossoms.

*Peduncle.*—Medium green in coloration, near Green Group 138B, approximately 2 cm in length.

*Pedicels.*—Approximately 1.5 to 2 cm in length.

*Sepals.*—Commonly extend beyond the bud and are pointed, and commonly approach Green Group 138B in coloration.

*Buds.*—Shape: initially pointed (as illustrated). Length: approximately 2.5 to 3 cm. on average. Color when opening: soft dark velvet red, Red Group 46B.

*Flower.*—Form: initially cup-shaped with flattening upon maturity. Appearance: velvety on both petal surfaces. Diameter: approximately 4 cm. on average. Color (when opening begins): Upper surface: primarily bright velvet red, Red Group 46B. Under surface: primarily bright velvet red, Red Group 46A. Color (when blooming): Upper surface: primarily bright velvet red, Red Group 46B, with the pollen and reproductive organs at the center becoming visible to provide attractively contrasting bright yellow coloration. Under surface: primarily Red Group 46A. Color (at end of opening): Upper surface: the velvet red coloration tends to change to near Red-Purple Group 74B just before the petals drop. Under surface: the velvet red coloration tends to change to near Red-Purple Group 74A just before the petals drop. Fragrance: none. Lasting quality: very good, with the blossoms commonly lasting approximately three days on the plant and approximately 2 to 3 days when cut and placed in a vase. Petal form: broad, fan-shaped, curved with a lightly indented central margin and the outer corners of the petals commonly are slightly pointed to the center. Petaloids: commonly none. Petal number: approximately 7 to 8 on average. Petal arrangement: generally arranged in a regular pattern with overlapping edges. Petal drop: good with a clean disengagement of the petals. Stamens: regularly arranged around the styles. Filaments: regularly arranged around the styles and are nearly transparent in appearance. Pollen: bright yellow in coloration (as illustrated). Stigmas: bright yellow in coloration, Yellow Group 6B (as illustrated). Styles: thin, regularly arranged around the center, and tend to be of substantially the same length. Hips: small, round, dark green in coloration which is near the colorations as that of the petals.

Development:

*Vegetation.*—Strong and vigorous.

*Blooming.*—In large sprays.

*Aptitude to bear fruits.*—Few in number unlike the 'Flower Carpet Yellow' variety (U.S. Plant Pat. No. 10,527).

*Winter hardiness.*—Good, and comparable to that of the 'Flower Carpet White' variety (U.S. Plant Pat. No. 9,573).

*Resistance to diseases.*—Excellent with respect to blackspot, mildew, and rust.

I claim:

1. A new and distinct variety of ground cover rose plant characterized by the following combination of characteristics:

(a) forms attractive dark velvet red blossoms with bright yellow pollen and reproductive organs at the center,
(b) exhibits a low, dense, compact and spreading growth habit,
(c) forms attractive glossy foliage that contrasts well with the dark velvet red blossoms,
(d) exhibits excellent disease resistance with respect to blackspot, mildew, and rust, and
(e) is particularly suited for growing as attractive ornamentation in the landscape;

substantially as herein shown and described.

* * * * *